United States Patent [19]

Kenny

[11] 4,220,386
[45] Sep. 2, 1980

[54] PLUG AND SOCKET CONNECTORS

[75] Inventor: John Kenny, Sawbridgeworth, England

[73] Assignee: Needle Industries Limited, Warwickshire, England

[21] Appl. No.: 884,830

[22] Filed: Mar. 9, 1978

[30] Foreign Application Priority Data

Mar. 10, 1977 [GB] United Kingdom ............... 10280/77

[51] Int. Cl.² ...................... H01R 11/18; A61N 1/04; H01R 13/52
[52] U.S. Cl. ............................. 339/60 R; 339/DIG.3
[58] Field of Search ............... 128/419 S; 339/60, 94, 339/DIG. 3

[56] References Cited

U.S. PATENT DOCUMENTS

| 2,379,942 | 7/1945 | Webber | 339/60 C |
|---|---|---|---|
| 2,704,355 | 3/1955 | Holton | 339/94 A |
| 3,002,126 | 9/1961 | Noir | 339/DIG. 3 |
| 3,344,391 | 9/1967 | Ruete | 339/60 R |
| 3,880,487 | 4/1975 | Goodman et al. | 339/60 R |
| 3,924,639 | 12/1975 | Hess | 339/DIG. 3 |
| 3,936,125 | 2/1976 | Hutter | 339/94 C |
| 4,033,355 | 7/1977 | Amundson | 128/419 P |
| 4,064,623 | 12/1977 | Moore | 339/DIG. 3 |
| 4,072,154 | 2/1978 | Anderson et al. | 339/94 C |
| 4,082,405 | 4/1978 | Stepniak | 339/DIG. 3 |

Primary Examiner—Paul A. Bell
Attorney, Agent, or Firm—Alexis Barron

[57] ABSTRACT

A plug and socket connector intended primarily for implantation in a human or animal body, for instance to connect an electrode catheter to a cardiac pacemaker casing. The plug member has an insulating body portion mounting a conducting spigot for connection to a conductor. The socket connector defines a bore in which the insulating body portion is received in a sealing manner. A block of conducting rubber material is positioned in the bore and has a recess in which the spigot is received, the cross-section of the recess being smaller than that of the spigot, so that the block is deformed as the spigot enters the recess, to make an electrical connection therewith. A contact extends through the wall defining the bore, to connect with the block. The conducting rubber may be a silicone rubber loaded with carbon particles.

9 Claims, 9 Drawing Figures

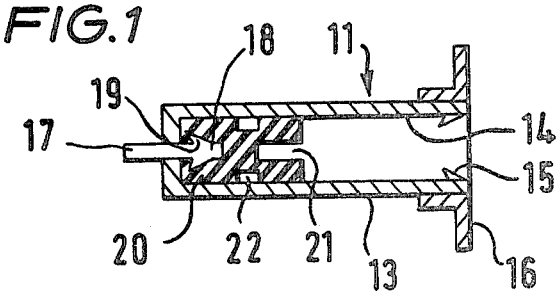
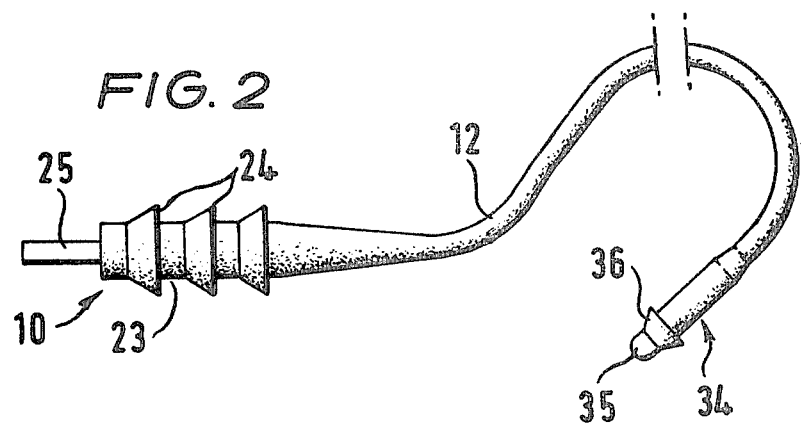
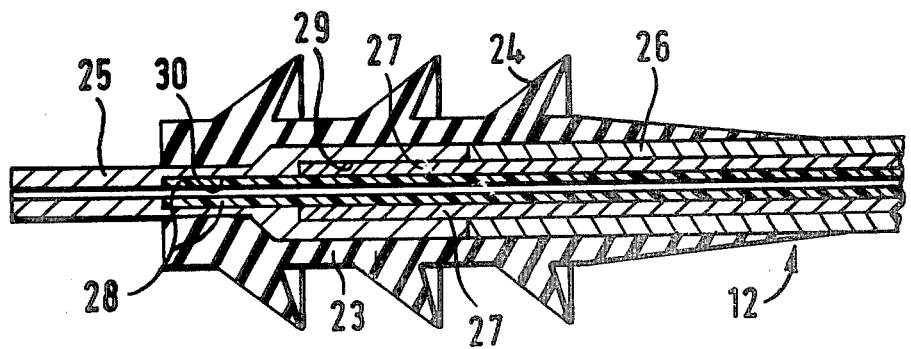

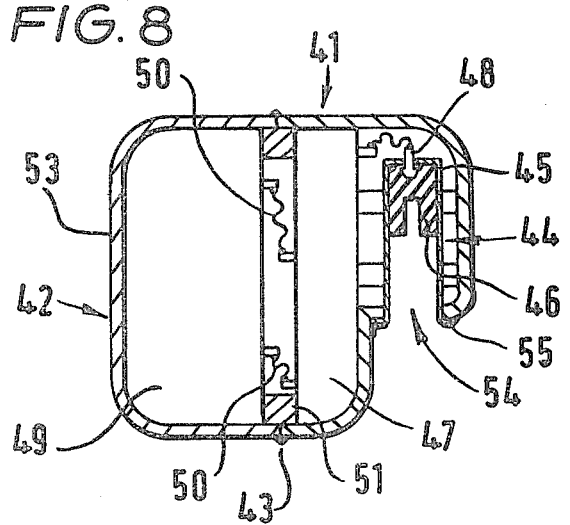
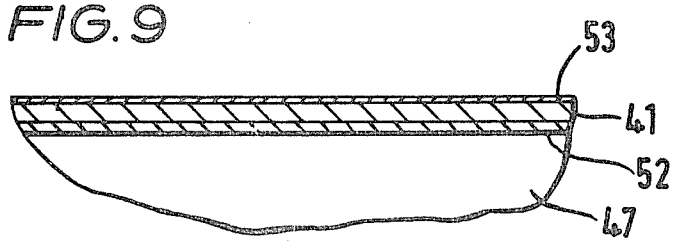
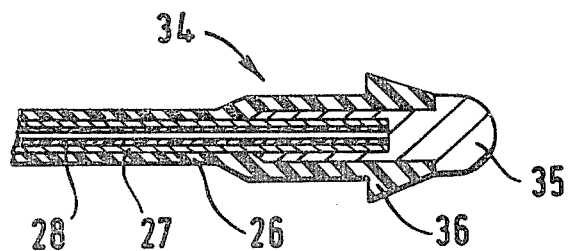

PLUG AND SOCKET CONNECTORS

BACKGROUND OF THE INVENTION (a) Field of the Invention

This invention relates to a plug and socket electrical connector, and in particular to such a connector which is suitable for implantation in an animal body. The plug and socket connector of this invention may be used with a cardiac pacemaker for implantation in a human body, to connect an electrode catheter (such as is described and claimed in my co-pending Application Ser. No. 884,967 filed on the same day as this Application in my name alone and entitled "Electrode Catheter", the entire disclosure of which is incorporated herein by reference) to a pacemaker (such as one constructed as described and claimed in my co-pending Application Ser. No. 884,966 filed the same day as this Application in my name alone and entitled "Cardiac Pacemakers" the entire disclosure of which is incorporated herein by reference).

(b) Description of the Prior Art

With an implanted cardiac pacemaker system, it is most important that the connection between the proximal end of the electrode catheter (the distal end of which communicates with the heart for stimulation thereof) and the implanted cardiac pacemaker (which normally is located some considerable distance from the heart) is very reliable and able to withstand the implanted environment for a considerable number of years. Not only must the connection offer very low electrical resistance, it must furthermore be hermetically sealed against the environment and body fluids at the site of implant. Spring-loaded metal-to-metal connectors together with fluid-tight seals have been used previously, but these have proved in practice to offer an increasing electrical resistance with time, owing to corrosion, and this can in turn lead to premature failure of the overall pacemaker system even though the life of the pacemaker itself has not expired.

OBJECTS OF THE INVENTION

It is a principal object of this invention to provide a plug and socket connector which is suitable for implantation in a body, which plug and socket connector is able to withstand the environment at the site of implantation for long periods of time. A further object is to provide a connector which is easy to connect and which, when connected, is reliable and provides a low contact resistance.

Another object is to provide a plug and socket connector, the plug member of which is suitable for provision on the end of an electrode catheter and the socket member is suitable for mounting within a cardiac pacemaker casing, whereby the catheter may be connected to the pacemaker casing.

SUMMARY OF THE INVENTION

In accordance with these and other objects, there is provided a plug and socket electrical connector especially useful for body implantable pacemakers, which connector comprises a plug member for electrical connection to a conductor and a socket member for receiving the plug member, the plug member having an insulating body portion and a conducting spigot projecting from said body portion and to which said conductor is connectible, the socket member having walls defining a bore for sealingly receiving said body portion of the plug member, a block of conducting, resilient, rubber material located within said bore, the block of rubber material defining a recess for receiving said spigot of said plug member, and an electrical contact provided through the walls of the socket member defining said bore and making electrical connection with the block of rubber material, said recess in said block of conducting rubber material having a smaller cross-sectional dimension than that of the spigot, whereby the block is deformed by insertion of said spigot into said recess to make an electrical connection therebetween.

BRIEF DESCRIPTION OF THE DRAWINGS

In order that the invention may better be understood it will now be described in greater detail and a specific embodiment thereof given by way of example, reference being made to the accompanying drawings. In the drawings:

FIG. 1 is a cross-sectional view through a socket member of a plug and socket connector arranged in accordance with this invention;

FIG. 2 is a side view of an electrode catheter including a plug member for use with the socket member of FIG. 1;

FIG. 3 is a cross-sectional view, but on an enlarged scale, through the plug member shown in FIG. 2, as fitted to an electrode catheter;

FIG. 6 is a cross-sectional view, but on an enlarged scale, through the distal end portion of the electrode catheter shown in FIG. 2;

FIG. 8 is a cross-section through the pacemaker casing of FIG. 7; and

FIG. 9 is a cross-section through the wall of the pacemaker casing of FIG. 7, but on an enlarged scale.

DETAILED DESCRIPTION OF THE PREFERRED ARRANGEMENTS

Figure 4:
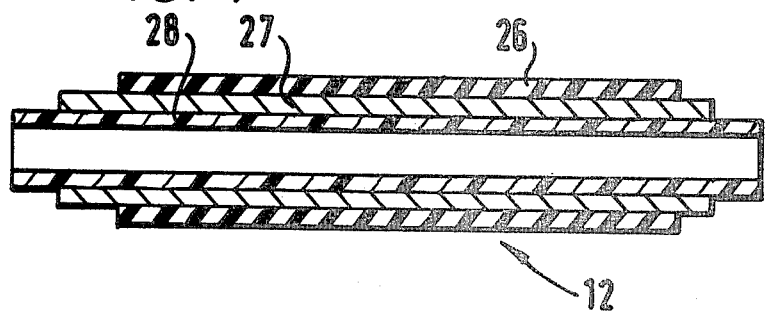
FIG. 4 is a cross-sectional view through part of an electrode catheter for use with the plug member of FIGS. 2 and 3.

The bore of the socket member is preferably circular in cross-sectional shape. The body portion of the plug member should therefore also be of circular cross-section and of such dimensions that the body portion is a sealing fit within the bore. Preferably, the body portion is resiliently deformable and, when relaxed, of a larger overall diameter than the bore of the socket member such that when the plug member is fitted within the bore of the socket member, the body portion is deformed to effect a fluid and gas tight seal against the wall of the socket member defining the bore. The plug member body portion conveniently is moulded from a natural or silicone rubber, and may be moulded directly on to the conductor.

To retain the plug member within the socket member, it is advantageous for the plug member to be provided with one or more projections such as ribs or barbs on its cylindrical body portion, which projections are directed away from the free end of the spigot whereby the plug member may with relative ease be pressed into the bore of the socket member but may be withdrawn therefrom only against the action of the projections. By forming the projections as annular barbs surrounding the body portion of the plug member, the barbs themselves may serve to enhance or form the sealing effect between the wall of the socket member defining the bore and the plug member.

Further to assist the retention of the plug member within the bore of the socket member, an inwardly-projecting annular rib may be provided within the bore, for engagement with the body portion of the plug member.

The conducting rubber material is preferably a silicone rubber which has been loaded with carbon particles—or a similar conductor—and such rubber is known per se. It exhibits excellent properties when a conductor displaying resilience or flexibility is required, and thus is used for instance for making contact pads for electrodes which must be maintained in contact with the skin of an animal or human body. The resilient properties of the material in all directions have proved valuable in this invention, in making an excellent electrical connection with the spigot of the plug member.

To ensure the rubber material is deformed on insertion of the spigot in the recess therefor in the block of conducting rubber material, the recess has a smaller cross-sectional dimension than the spigot. For instance, the recess could be of square and the spigot of circular cross-sectional shape, the side of the square being smaller than the diameter of the spigot. It is preferred however for the cross-sectional shapes of the recess and spigot to be the same, and conveniently circular, with the recess having a smaller diameter than the spigot. Then, as the spigot is driven into the recess, the rubber material is deformed to fit closely around the spigot and to make a low-resistance electrical connection therewith.

Preferably, the block of conducting rubber material is provided with at least one further recess or aperture spaced from the said recess for receiving the spigot, such that the deformation of the rubber material caused by the insertion of the spigot into the recess may be accommodated by a reduction in volume or change in shape of the further recess or aperture. In this way, the overall volume change of the conducting rubber material may be maintained at a minimum value as the spigot is inserted. The further recess or aperture may take the form of a radially outwardly facing annular channel located part-way between the ends of the block of rubber material.

The contact making an electrical connection with the block of conducting rubber material preferably is in the form of a metal stud having a barb-like head projecting into the bore and fitting within a correspondingly-shaped, but smaller, recess in the block of conducting rubber material such that the material is deformed to fit thereover. Conveniently, the wall of the socket member defining the bore is made of a ceramic material and the metallic stud—preferably of platinum—is provided in the wall during manufacture of the socket member so that a hermetic seal is formed therearound. Conveniently, a platinum flange is provided around the socket member adjacent the end of the bore through which the plug member is inserted, whereby the socket member may be sealed to the body or case of a piece of electrical equipment—for instance a cardiac pacemaker casing. Such sealing may be effected to create a hermetic seal, for example by an electron beam welding technique, and electrolytic corrosion may be avoided in this way. Platinum is selected for the flange and for the contact when employing a ceramic for the part of the socket member defining the bore because of the relative ease of forming a hermetic seal between a ceramic material and platinum.

The conductor to which the plug member is attached may take a variety of forms, but when the plug and socket connector are used in a pacemaker system, the plug should be attached to the proximal end of an electrode catheter, the distal end being appropriately positioned to stimulate the heart. Conveniently, the plug member may be moulded directly on the proximal end of such a catheter.

Referring initially to FIGS. 1 to 3, there is shown a plug and a socket connector intended for connecting an electrode catheter of a cardiac pacemaker system to a pacemaker casing. The connector comprises a plug member 10 and a socket member 11, the plug member 10 being moulded directly on the end of the electrode catheter 12 and the socket member 11 being adapted for incorporation in the casing of the pacemaker itself.

The socket member 11 (FIG. 1) comprises a main body 13 made from a ceramics material and defining a blind circular bore 14. An inwardly directed annular rib 15 is provided within the bore 14, spaced slightly from the open end thereof and upstanding from the wall defining the bore by about 0.1 mm. A circular metallic flange 16 (for instance of titanium) is provided on the ceramics body portion 13 around the open end of the bore 14 during the manufacture of the socket member, so that the flange 16 is hermetically bonded to the main body 13. Similarly, a conducting contact 17 is provided through the blind end wall of the main body 13 so as to project into the bore 14. The contact is conveniently of platinum, and is also hermetically sealed to the main body. Within the bore 14, the contact 17 has an enlarged head 18, provided with barbs 19 directed towards the blind end of the bore. Located within the bore 14 is a block 20 of relatively soft, resilient conducting silicone rubber material, loaded with carbon particles to render the block electrically conducting. The block 20 is generally of circular cross-section to fit closely within the bore 14, and has a circular recess 21 opening co-axially towards the open end of the bore 14. A second co-axial recess is provided for receiving the head 18 of the contact 17, the block 20 being deformed to fit over the head and engage with the barbs 19, thereby making a good electrical connection therebetween. An annular channel 22 is provided partway between the ends of the block 20 of conducting silicone rubber material.

The conducting silicone rubber material is known per se and comprises relatively soft, resilient silicon rubber which has been loaded with carbon black. Such material displays reasonable electrical conductivity, though the resistance offered depends to some extent upon the degree of compression of the material. A typical material is that known as Dow-Corning Q4-1602 Silastic.

The plug member 10 (FIGS. 2 and 3) comprises a body portion 23 of circular cross-section and is provided with three annular ribs 24, each having the general cross-sectional shape of a barb directed generally away from the free end of the plug member 10. The body portion 23 is moulded from insulating silicone rubber, and is thus flexible, relatively soft and resilient. The material is similar to that of the block 20, except that it has not been loaded with carbon black; as such the material displays excellent insulating properties. A typical material for this purpose is that known as Dow-Corning MDX-4-4210 Clean-Grade Elastomer. The body portion 23 is moulded around a metal spigot 25, which projects from the free end of the body portion for connection with the socket member of FIG. 1. The diameter of the spigot 25 should be slightly greater than that of the recess 21 when the block of silicone rubber is located in the bore 14 of the socket member 11.

As shown in FIG. 3, the body portion 23 is moulded directly on to an electrode catheter 12, which is described in detail below. The catheter 12 includes an outer insulating silicone rubber protective sleeve 26, conductors 27 and a plastics core 28. The spigot 25 is shaped to receive in a first counterbore 29 the conductors 27, to make electrical connection therewith, and in a second, smaller counterbore 30 the plastics core 28. The body portion 23 bonds during the moulding operation to the sleeve 26, and if required the spigot 25 can lightly be crimped on the conductors 27 to ensure a reliable electrical connection thereto.

In use, when the plug member 10 is fitted into the socket member 11, the spigot 25 enters the recess 21 in the block 20 of conducting silicone rubber located within the bore 14 and makes an electrical connection therewith. By arranging the diameter of the recess 21 to be of slightly smaller size than that of the spigot 25, the rubber is compressed and resiliently urged into engagement with the spigot, as the spigot enters the recess 21 and a good electrical connection is thereby achieved. The annular channel 22 allows the rubber to distort and deform as required to allow accommodation of the spigot 25 in the recess 21. The annular ribs 24, shaped as barbs, allow the body portion 23 of the plug member easily to enter bore 14 of the ceramic body 16 but restrain withdrawal of the plug member owing to their barb-like shape. The rib 24 nearest the catheter 12 rides over and engages behind rib 15 of the socket member 11, and further assists in the retention of the plug member within the socket member. Moreover, the ribs 24 of the plug member 10 effect a hermetic seal between the body portion 23 of the plug member and the main body 13 of the socket member, whereby the electrical connection between the spigot 25 and the block 20 of conducting silicone rubber material is isolated from the surrounding environment.

Figure 5:
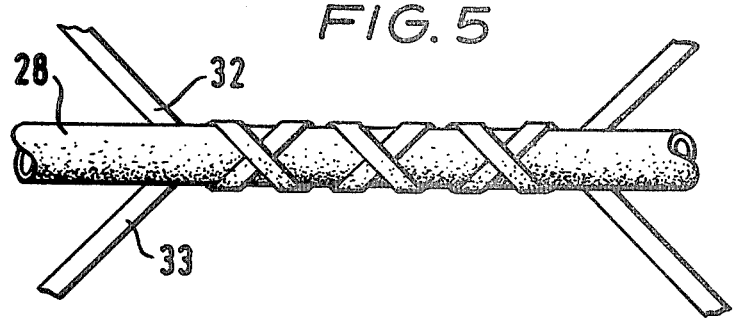
FIG. 5 is a diagram showing the fabrication of the catheter of FIG. 4.

Referring now to FIGS. 3 to 6, there is shown an electrode catheter 12 intended for use in a cardiac pacemaker system, connectible by means of the plug and socket connector described above to a pacemaker casing, and having an electrode for heart stimulation at its distal end. The catheter comprises a flexible, hollow core 28 of insulating plastics material such as polypropylene over which is laid a plurality of carbon-fibre monofilament conductors 27, each of approximately 10μ diameter. The carbon-fibre monifilament conductors 27 are assembled together into two groups 32 and 33 each containing several hundred such monofilaments randomly-oriented—and typically from 200 to 1000—and the two groups are then wave-wound around the core 28 as shown in FIG. 5. In this way, the groups are interwoven around the core 28 to form an open net-like tubular structure extending along the plastics core 28.

Extruded over the core 28 carrying the wave-wound groups of monofilament conductors 27 is a protective, insulating sleeve 26, of insulating silicone rubber material. By extruding the silicone rubber sleeve 26 directly as a tube over the carbon-fibre monofilament conductors 27, the sleeve is moulded around the groups of filaments as well as the filaments themselves such that they are partially embedded in the sleeve. In this way, the sleeve serves to retain the conductors 27 in the required position, as well as protecting the conductors against damage and insulating the conductors from the surroundings.

The electrode catheter described above has a relatively low impedance with good flexibility, whilst displaying excellent torsional rigidity (owing to the plastics core 28) allowing the catheter to be inserted where required within an animal or human body. The silicone rubber sleeve is virtually inert and is essentially biocompatible within human or animal bodies.

Though distal end of the catheter should be terminated in an appropriate manner for the intended use of the catheter, and such terminations—for instance for cardiac stimulation—are well known in the art.

FIG. 6 shows the electrode 34 provided at the distal end of the electrode catheter. This electrode comprises a platinum tip 35 having a rounded free end, there being an axial bore extending into the tip from its other end. In this bore are received the plastics core 28 and the carbon-fibre conductors 27 such that the conductors are connected electrically to the tip 35. The silicon rubber sleeve 26 is moulded directly over part of the tip 35 so as to insulate the greater part thereof and to hold the tip on the core and conductors. A silicone rubber flange 36 is provided at the end of the sleeve 26 so as to assist retention of the electrode in the required position.

Figure 7:
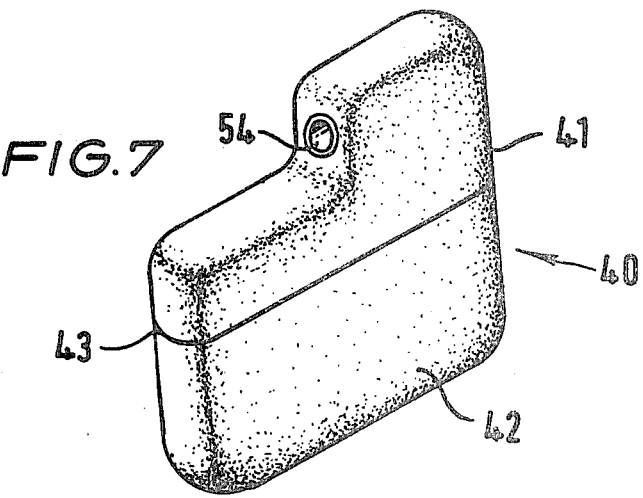
FIG. 7 is a perspective view of a cardiac pacemaker casing incorporating the socket member shown in FIG. 1.

FIGS. 7 to 9 show a cardiac pacemaker implant case 40, embodying a socket member generally similar to that shown in FIG. 1 and for use with a catheter electrode having a plug member as shown in FIG. 3.

The case for the pacemaker comprises two separate moulded plastics chamber parts 41 and 42, which mate together at 43 to define a complete chamber. Part 41 is fitted with a socket member 44, comprising a ceramic body 45 defining a bore in which is located a conducting silicon rubber block 46, connected to an electronic package 47 contained within chamber part 41 by means of contact 48 extending through the ceramic body 45. Within the chamber part 42 is a battery pack 49, connected to the electronic package 47 by means of wires 50. A continuous ring 51 of resilient silicone rubber material is positioned between the electronic package 47 and the battery pack 49 so as to urge the package and pack 47 and 49 respectively apart, into firm engagement with the associated chamber parts 41 and 42. The ring 51 moreover is engaged with the chamber parts 41 and 42 immediately under the mating region 43 of the chamber parts. If required, as shown in FIG. 9, a layer 52 of silicon rubber can be provided between the inner wall of a chamber part and the package or pack therewithin. The two chamber parts 41 and 42 can be glued together once all the components have been assembled therewithin, by means of an adhesive selected for the plastics material of the chamber parts. For instance, the parts can be of an epoxy resin, and a similar resin used for glueing the parts together.

The entire moulded plastics chamber parts 41 and 42 are covered by a platinum skin 53, also formed in two separate parts which abut in the mating region 43 of the two chamber parts. The skin is shaped from platinum sheet of about 0.25 mm thickness, so as to fit closely over the chamber parts. An aperture 54 is provided in the skin around the opening into the bore of the socket member 44. The abutting edges of the two separate parts of the skin 53 are welded together by an electron beam welding technique and the skin is also welded around the aperture 54 to a metal flange 55 around the socket member 44 by the same technique, whereby a continuous, hermetical seal is formed around the entire casing.

The two parts of the platinum skin conveniently are formed by a deep drawing operation from a flat sheet of platinum, using the chamber parts themselves as the male drawing tool. Pure platinum is relatively soft and lends itself to such a forming operation, especially when in a relatively thin sheet, particularly because the material displays virtually no spring-back. However, the skin could be formed separately and then fitted to the assembled chamber parts prior to the welding operation.

An electrical connection must be provided to the platinum skin, to allow a current return from the distal end of a catheter used with the pacemaker case. Conveniently, this is effected by means of the flange 55 of the socket member 44, connected internally back to the electronic package 47 within chamber part 41.

In use, an appropriate electrode catheter fitted with a plug member at its proximal end for insertion into socket member 44 is introduced into the body so that the distal end is within the heart where stimulation is required, and the proximal end is adjacent the site of implanting of the pacemaker case. If a catheter such as is described above is used, excellent torsional control of the distal end can be achieved by operation—and principally rotation—of the proximal end during positioning of the distal end. Next, the plug member 10 of the catheter is inserted into the socket 40 of the pacemaker casing, and the pacemaker is positioned suitably at the implantation site, whereafter the surgery is completed in the usual way.

It is found that the platinum skin, even though serving as a contact for the earth return, is not prone to corrosion or other deterioration, for platinum proves to be virtually inert within the environment of a human or animal body at the usual sites of implantation. Thus the life of the implanted pacemaker will be dictated by the battery pack 49, rather than by the life of the pacemaker casing or the life of the electrode catheter—and battery packs are currently being produced which should call for preventative replacement only every 5 years, even though the actual life may be yet longer.

What is claimed is:

1. A plug and socket electrical connector, which connector comprises a plug member for electrical connection to a conductor and a socket member for receiving the plug member, the plug member having an insulating body portion and a conducting spigot projecting from said body portion and to which said conductor is connectible, the socket member defining a bore for sealingly receiving said body portion of the plug member, a block of conducting resilient rubber material located within said bore, the block of rubber material defining a first recess for receiving the spigot of said plug member and defining a further recess spaced from said first recess for receiving the spigot, and an electrical contact provided through the walls of the socket member defining said bore and making electrical connection with said block of rubber material, and said first recess in said block of conducting rubber material having a smaller cross-sectional dimension than that of said spigot, whereby the block is deformed by insertion of said spigot into said first recess to make an electrical connection therebetween, said deformation of the block of rubber material caused by insertion of said spigot into said first recess being accomodated at least in part by a reduction in volume of said further recess.

2. A connector as claimed in claim 1, in which said conducting rubber material comprises a silicone rubber loaded with carbon particles.

3. A connector as claimed in claim 1, in which said bore defined by the socket member and said body portion of the plug member are of circular cross-sectional shape, and said body portion is resiliently deformable and when relaxed of a larger overall diameter than said bore defined by said socket member whereby said body portion is deformed as the plug member is fitted within said bore to effect a seal against the walls of the socket member defining said bore.

4. A connector as claimed in claim 1, in which said plug member is provided with one or more projections on the outer surface of the body portion, which projections are in the form of annular barbs directed away from the free end of the spigot.

5. A connector as claimed in claim 1, in which an inwardly-projecting annular rib is provided within said bore for engagement with said body portion of the plug member.

6. A connector as claimed in claim 1, wherein the cross-sectional shapes of said first recess and said spigot are circular, with said first recess having a smaller diameter than the spigot.

7. A connector as claimed in claim 1, in which said contact making an electrical connection with said block of conducting rubber material is in the form of a metal stud, a barb-like head being provided on said stud and projecting into said bore, said block of conducting rubber material defining a third recess the shape of which corresponds to that of said barb-like head but of a smaller size such that accommodation of said barb-like head in said third recess deforms said rubber material to make electrical connection with said contact.

8. A plug and socket electrical connector, which connector comprises a plug member for electrical connection to a conductor and a socket member for receiving the plug member, the plug member having a resiliently deformable body portion of circular cross-sectional shape, at least one annular projection in the form of a barb upstanding from said body portion, a spigot projecting axially from said body portion and to which said conductor is connectible, the socket member defining a bore of circular cross-section and of a diameter smaller than that of said resiliently deformable body portion of said plug member, a metal stud provided through the walls of the socket member defining said bore, an enlarged barb-like head being provided on said stud within said bore, and a block of resiliently deformable, conducting silicone rubber material loaded with carbon particles provided within said bore, said block defining an axial first recess for receiving said spigot, said first recess having a smaller cross-sectional dimension than that of said spigot, and said block further defining a second recess for receiving said barb-like head of said stud, said second recess being of the same shape as but of smaller size than said head and said block yet further defining a third recess in the form of an annular channel part-way between ends of said block which third recess accommodates deformation of said block caused by insertion of said plug member into said socket member thereby driving said spigot into said axial first recess.

9. A connector as claimed in claim 8, in which said socket member comprises walls formed of a ceramic material to define said bore, a platinum stud extending through said walls to connect to said block of conducting rubber material, and a metallic mounting flange selected from the group consisting of titanium and platinum bonded to said walls around the opening to said bore.

* * * * *